(12) United States Patent
Hnasko et al.

(10) Patent No.: US 11,415,578 B2
(45) Date of Patent: Aug. 16, 2022

(54) BIOSENSOR PLATFORM FOR RAPID DIAGNOSTIC TESTING

(71) Applicant: The United States of America, as represented by the Secretary of Agriculture, Washington, DC (US)

(72) Inventors: Robert M. Hnasko, Pinole, CA (US); Eric S. Jackson, Lafayette, CA (US); Ronald P. Haff, Davis, CA (US); Susan Uramoto, Novato, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 474 days.

(21) Appl. No.: 16/444,235

(22) Filed: Jun. 18, 2019

(65) Prior Publication Data
US 2020/0400661 A1 Dec. 24, 2020

(51) Int. Cl.
*G01N 33/543* (2006.01)
(52) U.S. Cl.
CPC ............... *G01N 33/54366* (2013.01)
(58) Field of Classification Search
None
See application file for complete search history.

(56) References Cited

U.S. PATENT DOCUMENTS

| | | | |
|---|---|---|---|
| 6,316,205 B1 | 11/2001 | Guan et al. | |
| 7,032,632 B2 | 4/2006 | Shingle et al. | |
| 7,090,803 B1 * | 8/2006 | Gould et al. | G01N 33/558 422/413 |
| 2004/0184954 A1 | 9/2004 | Guo et al. | |
| 2010/0112604 A1 | 5/2010 | Drawdy | |

* cited by examiner

*Primary Examiner* — Kaijiang Zhang
(74) *Attorney, Agent, or Firm* — John Fado; Robert Jones

(57) ABSTRACT

The bio sensor platform is a rapid point-of-care (POC) device wherein detection of a target analyte from a liquid or solid substrate is performed in a single step using a fully integrated disposable test system that includes a test strip immunoassay. In operation, a user initiates the test by rupturing the bottom of a liquid-filled analyte capsule seated in a capsule sleeve. A small volume of liquid flows by capillary action from the capsule sleeve and through a restrictor port to a test strip chamber where contact with the absorptive sample pad of the test strip (among other things) moves liquid by capillary action upwardly through the test strip. The detection of the target analyte is resolved by the test strip reagents and the test results are obtained at a test result window where a portion of the test strip is exposed to the user.

22 Claims, 11 Drawing Sheets

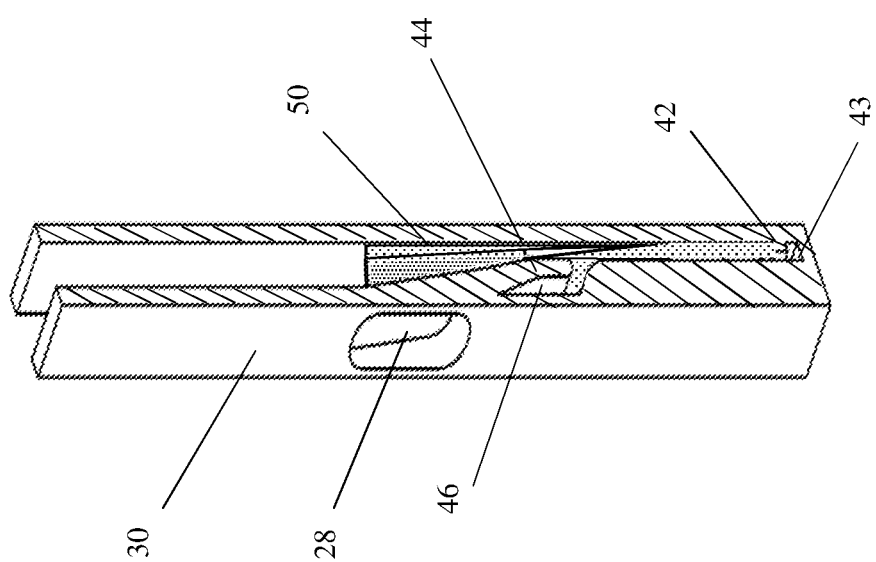
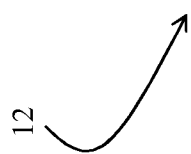
FIG. 6

BIOSENSOR PLATFORM FOR RAPID DIAGNOSTIC TESTING

FIELD OF THE INVENTION

The disclosed method and system relates to a single-use biosensor platform designed to perform a rapid immunoassay. The system uses modular components that enable users to perform simple point-of-care (POC) tests in a portable setting. Specifically, the method and system described herein relates to a modular biosensor platform that fully integrates all the necessary assay components in a small single-use disposable platform for the rapid detection of analytes from either solid or liquid substrates using an immunoassay test strip format.

BACKGROUND OF THE INVENTION

There is an expanding demand for rapid POC testing in the general health and food safety areas. These types of tests can provide inexpensive and easy-to-use detection options for allergens, pathogens, toxins, adulterants and other environmental contaminants from the farm to the fork. Based on current data, the market for these types of tests is projected to expand at a rate of about 10% annually—and eventually grow to more than $38 billion by 2022. North America accounts for the greatest share of the market at a projected market size of $16B, with the largest growth occurring in lateral flow assays, detection of infectious diseases, and 'at home' and personal end-user health management segments.

The most successful lateral flow devices (to date) include detection of human chorionic gonadotropin (hCG), a hormone associated with human pregnancy, and assays that detect the presence of specific (usually illicit) drugs in the system of a test subject. These assays utilize direct liquid urine samples and consequently device designs do not require a liquid sample extraction buffer and precision liquid delivery mechanism.

Many applicable tests, particularly in agriculture, require extraction of solid into a liquid or the pH buffering of a liquid sample coupled to a mechanism to deliver a limited volume with precision to a test strip for testing to proceed. To achieve this, current state of the art lateral flow devices provide separate poorly integrated components relying on multi-step procedures to perform simple tests.

These assay kits often include: 1) an immunochromatographic test strip in a two-piece plastic housing stored dry in a desiccant bag; 2) a separate container with liquid sample extraction buffer; and, 3) a disposable liquid transfer pipette. The tests proceed after the end-user transfers a volume of liquid from the sample extract to a sample port on the test strip housing in a horizontal orientation. End-user error in liquid delivery volume and/or location is a significant problem. Moreover, multi-step science-kit methodologies are frequently impractical, prone to error, cumbersome to perform and therefore less desirable to end-users in field locations.

To address these issues, the inventors have developed a modular bio sensor platform that integrates an immunoassay test strip with sample extraction and liquid delivery in a small, easy-to-use and disposable format. This biosensor platform provides users with rapid and accurate test results in a single-step with minimal end-user training. The inventors' flexible biosensor platform is comprised of a small field portable unit that provides a stand-alone test that includes fully integrated sample extraction capability and liquid delivery to immunochromatographic test strips.

This bio sensor system is suitable for the rapid detection of target analytes from a wide range of liquid and solid substrates and is compatible with most standard lateral flow test strip dimensions. Components of the modular biosensor platform are designed for ease of manufacturing and assembly allowing interchangeable components to accommodate different test and liquid extraction buffer combinations. The inventors' modular biosensor platform is designed to be compatible with a separate digital reader tool that allows rapid digital porting of test strip results onto a data platform for recording and analyzing the resulting test data.

SUMMARY OF THE INVENTION

This disclosure is directed to a modular biosensor system that is used to test for the presence or absence of a target analyte in a substrate. The system includes a test receptacle comprising an outer sleeve, and a test capsule containing a liquid. The sleeve includes a central opening structured to hold a liquid filled capsule, and a test strip chamber configured to hold a standard immunochromatographic test strip.

The base of the sleeve includes a restrictor port which allows liquid to flow from the sleeve central opening to the test strip chamber. The sleeve also includes a resilient flex plate that extends into the test strip chamber and abuts the test strip.

In operation, a user adds a sample to the liquid filled capsule and initiates a test by rupturing the capsule. The analyte liquid flows out of the capsule, through the restrictor port and into a bottom portion of the sleeve. The restrictor port—in combination with the test strip chamber and a bottom portion of the test strip, forms a structural relationship that functions to create a capillary force that wicks the analyte from the bottom of the sleeve, through the restrictor port and up the test strip. As the analyte moves up the test strip, the flex plate holds the test strip in position and maintains material contact allowing the analyte to move upwardly through the test strip and transfer between test strip materials. The user reads the test results through a test window opening which allows the user to see the results shown on a top portion of the test strip.

BRIEF DESCRIPTION OF THE DRAWINGS

FIG. 6 is a perspective sectional of the front portion of the sleeve.

DETAILED DESCRIPTION OF PREFERRED EMBODIMENTS

Figure 1:
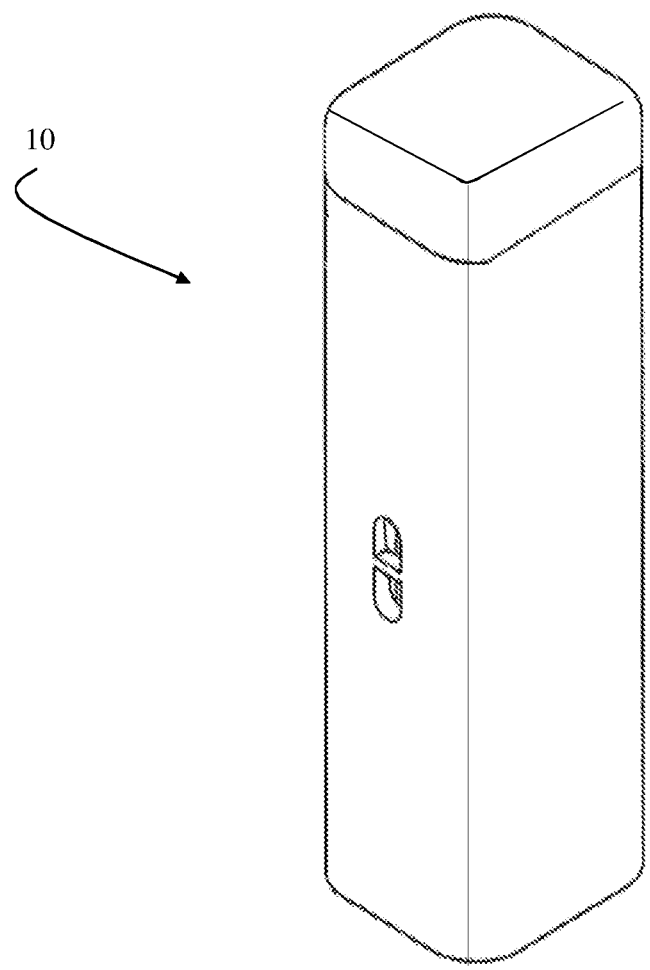
FIG. 1 is an elevational perspective view of the assembled biosensor system.

As generally shown in FIG. 1, the system described herein comprises an integrated modular biosensor 10. FIG. 1 shows one embodiment of the modular biosensor system 10 in the fully assembled configuration.

Figure 2:
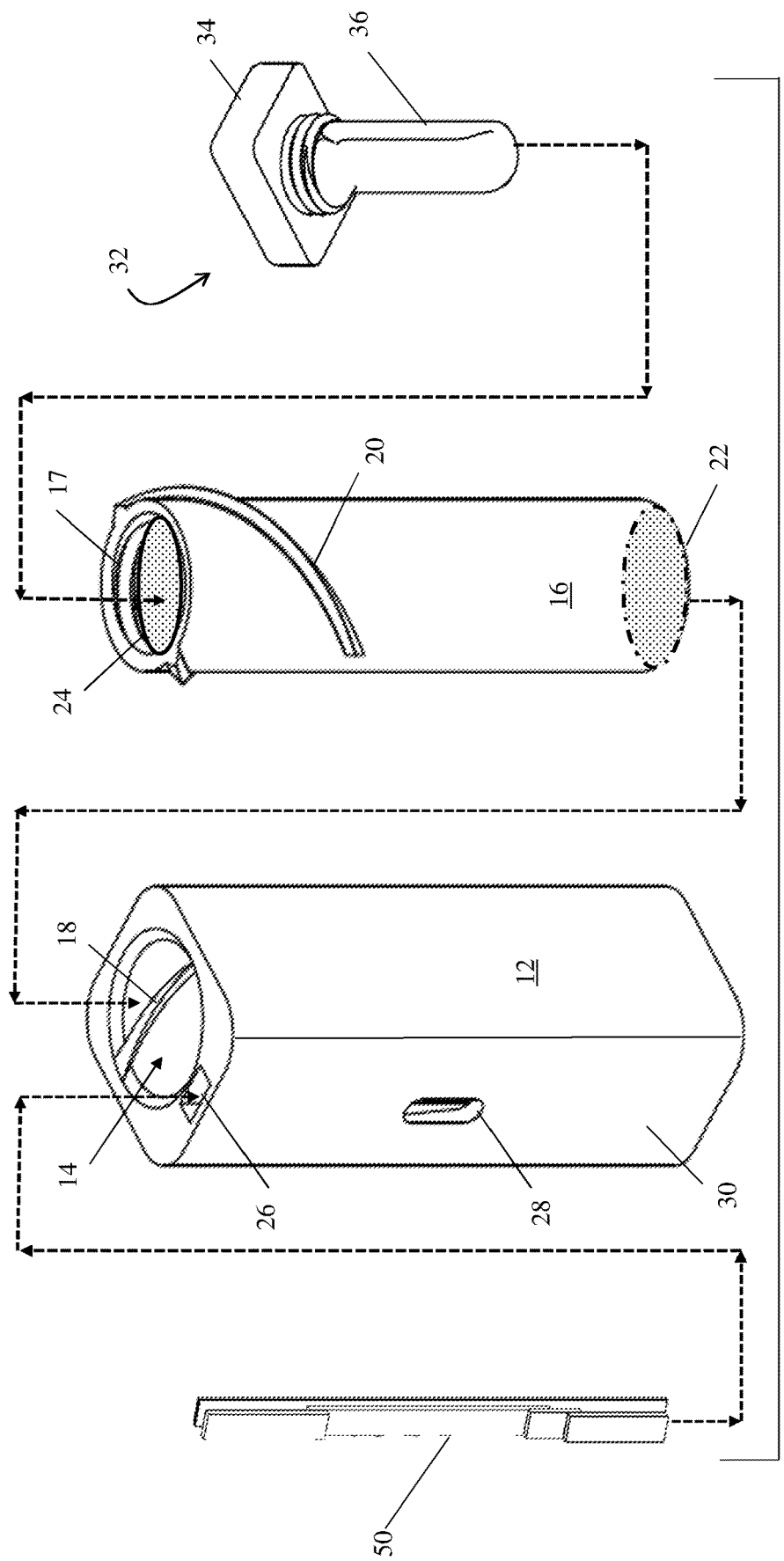
FIG. 2 is an exploded/assembly view of the biosensor system.

FIG. 2 shows an assembly/exploded view of the modular bio sensor system 10. As shown in FIG. 2, the system 10 comprises a capsule sleeve 12 with a central interior opening 14 of sufficient size to accommodate a cylindrical watertight liquid capsule 16. The capsule 16 includes an open top end 24 and a frangible bottom 22. The top end 24 may be open, or the top end 24 may also be covered by a modular frangible adaptor or cap 32. The capsule 16 may be empty or the capsule 16 may be pre-filled with a buffering liquid, or the liquid may comprise any fluid known in the art consistent with needs of a user, and the physical limitations of the capsule 16.

In the preferred embodiment, as best shown in FIGS. 1 and 2, the sleeve 12 is generally cubic with a vertical height of 63 mm, a horizontal width of 20 mm, and a horizontal length of 22 mm. The capsule 16 has a cylindrical shape with a height in the range of 55 mm, and a diameter in the range of 7 mm. However, in alternative embodiments, the dimensions of the components 12 and 16 may be modified to meet the needs of an individual user.

In the preferred embodiment, the sleeve 12 central opening 14 includes an interior screw thread 18 that corresponds to an exterior screw thread 20 on the analyte liquid capsule 16. A user must screw the capsule 16 down into the central opening 14 of the sleeve 12 to initiate a test. The necessity to screw the capsule 16 down into the sleeve 12 prevents the test process from being inadvertently initiated until the user is ready to begin the test. Essentially, the test will not begin until a user has taken a positive intentional action by screwing the capsule 16 into the sleeve 12 central opening 14. When the test is initiated, the sleeve 12 holds the capsule 16 in a generally vertical position for the duration of the test.

As further shown in FIG. 2, the capsule 16 includes threads 17 configured to receive a cap 32. The cap 32 comprises an upper portion 34 that is visible above the sleeve 12, and a lower portion 36 that may comprise a scoop or other tool-type mechanism. In alternative embodiments, the lower portion 36 of the cap 32 may comprise a variety of tools including a spoon, spatula, grinder, paddle, fork, knife, plug, a punch, a measuring device, a filter, or any other sampling/utility tool that can be contained within the capsule 16. The tool comprising the lower portion 36 of the cap 32 may function to cut or otherwise remove or gather material to be added to the capsule 16. In the preferred embodiment, the cap 32 is a standard size, and the configuration of the cap 32 is based on the needs of a user.

In addition to a cap 32, the threads 17 may be configured to receive a flow adaptor or tubing connection so that fluid can be easily made to flow through the cap 32 and into the capsule 16. The threads 17 may comprise a snap lip-type connector or any other connecting means required to connect the capsule 16 with a desired attaching top/mechanism. Alternatively, the upper portion 34 of the cap 32 may be comprised of a resilient material so that a needle can penetrate the cap 32 and inject a fluid directly down into the capsule 16.

The capsule sleeve 12 also includes a narrow, elongated test strip sleeve/chamber 26 designed to accommodate a standard paper test strip 50 that is (preferably) 4-5 mm in width and about 60 mm in length. The test strip chamber 26 is positioned in a front wall 30 of the sleeve 12 and extends the majority (62 mm) of length of the sleeve 12. In operation, a user slides the test strip into the test strip chamber opening 25 and continues to slide the test down into the test strip chamber 26 until the bottom of the test strip 50 abuts a test strip stopper 42. The test strip stopper 42 comprises a pair of pins that support the bottom corners of the test strip 50. The test strip stopper pins may extend horizontally outward from a wall of the test strip chamber 26. In alternative embodiments, the test strip stopper pins 42 may extend upwardly from the bottom 41 test strip chamber 26.

The test strip 50 is preferably comprised of industry standard materials such as plastic-backed nitrocellulose and specialized layered paper/media containing analyte detection reagents and other chemical indicators, as required for a specific test. In the preferred embodiment, the test strip comprises at least a sample pad, 46, a conjugate release pad 47, and a nitrocellulose membrane 48 (see FIG. 7). In alternative embodiments, the test strip 50 may be comprised of any material known in the art. In one (simple) embodiment, the test strip 50 utilizes antibodies that specifically recognize and bind a target substance conjugated to a molecular reporter such as gold nanoparticles. Single substance detection can include a target-specific antibody striped on a nitrocellulose substrate at a test line (T) and an appropriate target analyte independent antibody striped at a control line (C).

The capsule sleeve 12 also includes a test result window 28 on the capsule sleeve's front panel 30. The test window 28 comprises an aperture in the front panel 30 of the sleeve 12. The test window 28 is positioned so that a user can see a designated portion of the test strip 50 positioned in the test strip chamber 26. An observer can directly read the read the results of the test from the test strip 50 through the test window 28. Alternatively, the test window 28 may be configured so that a digital test result reader can read the test results digitally.

FIGS. 3-7 show the interior components of the outer sleeve 12. The bottom 41 of the central opening of the sleeve 12 includes an angular spike 38 that functions to puncture or break the bottom of capsule 16 when the user twists the capsule 16 into place, and thereby liberate the liquid in the capsule 16. In alternative embodiments, the "spike" 38 may comprise any configuration consistent with the function of piercing the test liquid analyte capsule 16. In further alternative embodiments, the capsule 16 may simply slide into the sleeve 12 without the use of a threaded connection 18, 20, or there may be a snap lip-type receiver in the bottom 41 of the central opening of the sleeve 12, or another means of mating and locking the capsule 16 into the bottom 41 of the sleeve 12.

Figure 3:
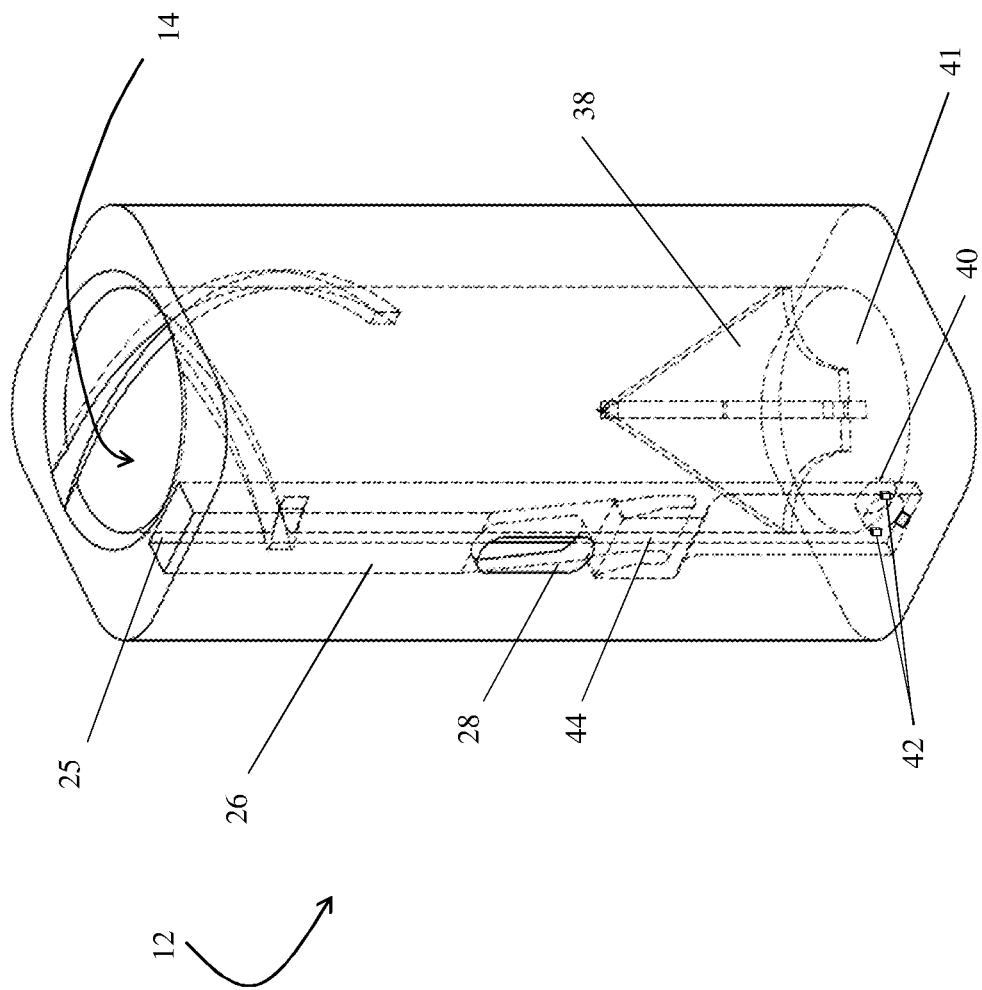
FIG. 3 is an elevational hidden line drawing showing the internal components of the capsule outer sleeve.
Figure 4:
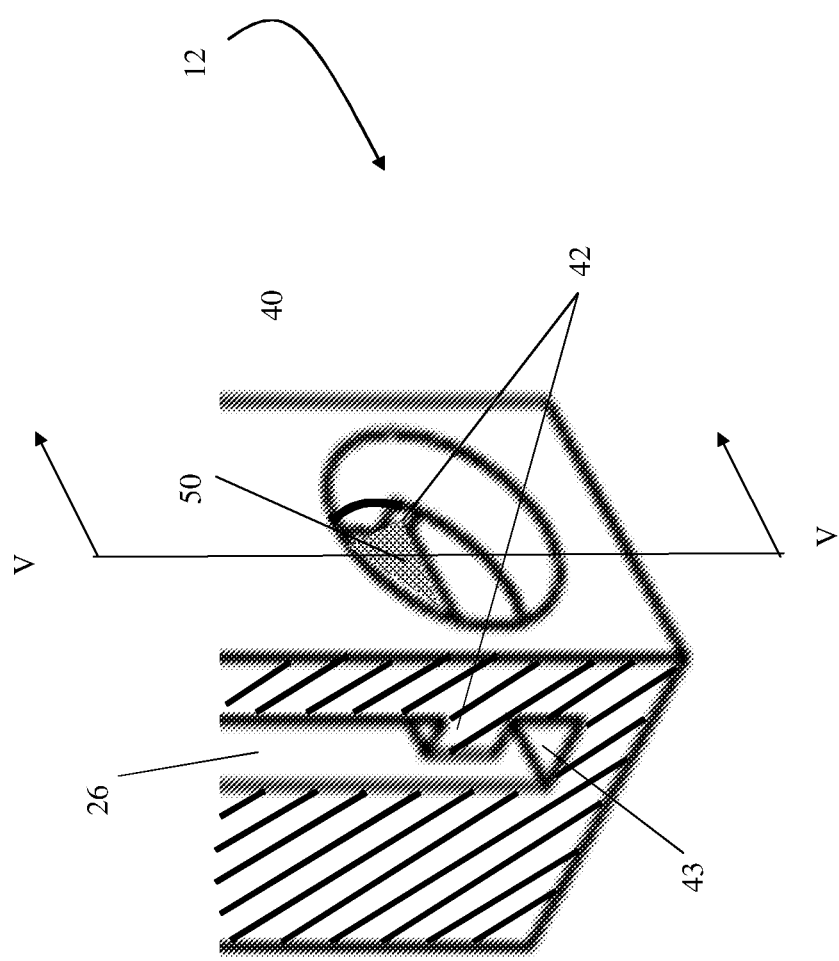
FIG. 4 is a perspective sectional view of the bottom portion of the sleeve, including the section line V-V.
Figure 5:
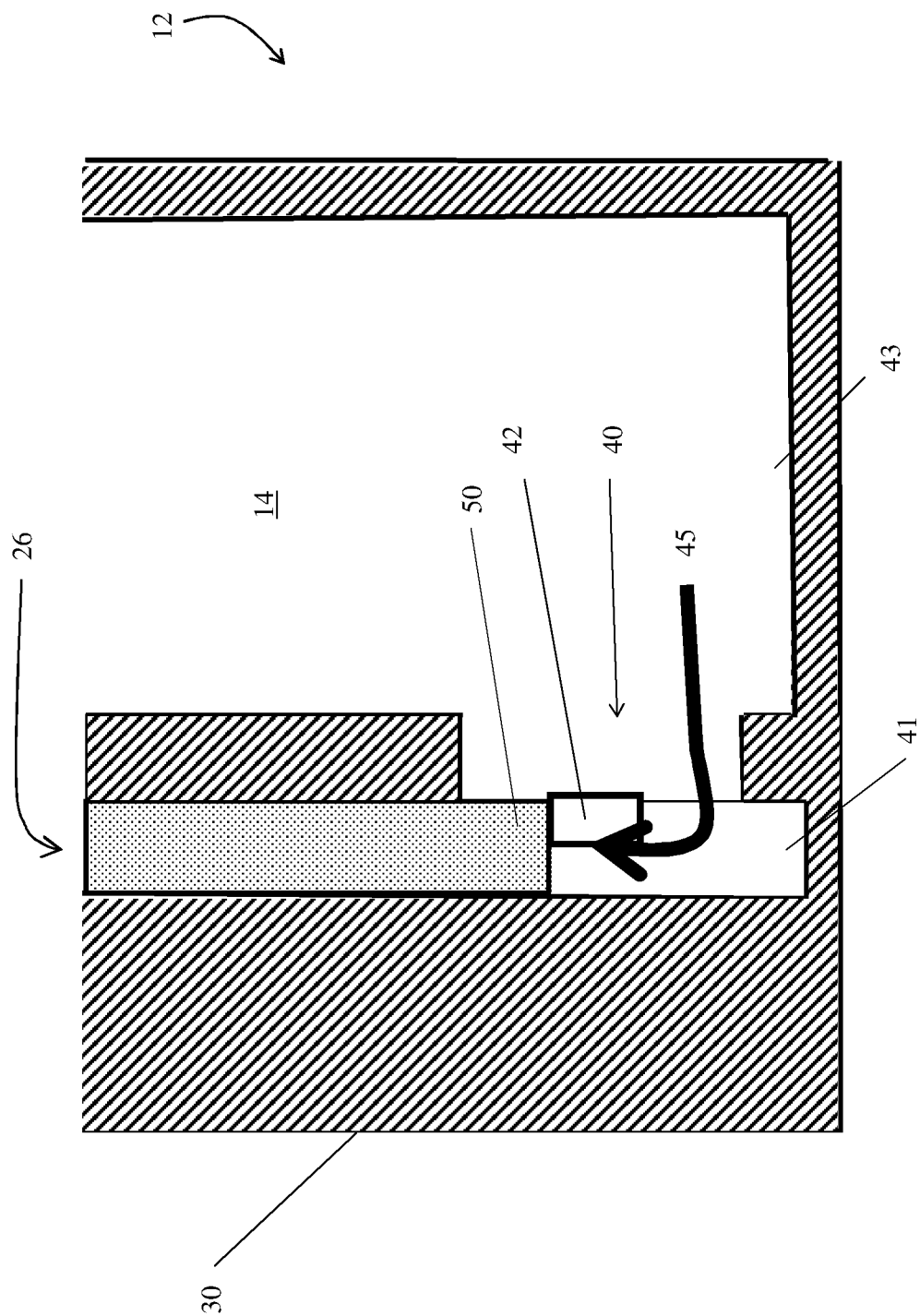
FIG. 5 is a sectional view of the bottom portion of the sleeve along the section line V-V shown in FIG. 4.

FIGS. 3, 4, and 5 show a restrictor port 40 positioned near the bottom 43 of the test strip chamber 26. The restrictor port 40 connects the test strip chamber 26 to the central interior opening 14 of the sleeve 12. More specifically, as best shown in FIGS. 4 and 5, the restrictor port 40 connects the bottom 43 of the test strip chamber 26 to the bottom 41 of the central opening 14 of the sleeve 12. In the preferred embodiment, the restrictor port 40 has a diameter of 3 mm. The size and placement of the restrictor port 40 are crucial to the ability of a user to conduct an accurate test. The restrictor port 40 is designed to modulate and control movement of the analyte fluid from the capsule 16 to the test strip 50.

Specifically, as best shown in FIG. 5, the restrictor port 40—in combination with the test strip chamber 26 and the bottom portion of the test strip 50—forms a structure that functions to create a capillary force wicking (as indicated by the arrow 45) fluid from the central interior opening 14 through the restrictor port 40 and upwardly to the test strip 50. The test strip 50 then "wicks" (via capillary action) the fluid up to the test window 28—which corresponds with the portion of the test strip 50 indicating the results of the test.

In the preferred embodiment, the test fluid is water-based or has fluidic properties that are similar to water. In alternative embodiments, the fluid may comprise alcohol, acids, bases, or any other substance consistent with the capability of capillary action-type movement.

The bottom end of the test strip 50 rests on the test strip stopper 42, which maintains the position of the test strip 50 above the bottom 43 of the test strip chamber 26. As shown in FIG. 3, the test strip stopper 42 extends horizontally from an inner wall of the test strip chamber 26. As best shown in FIG. 4, the test strip 50 abuts and partially covers/obstructs the restrictor port 40 so that the fluid contacts the test strip 50 as the fluid flows through the restrictor port 40. The placement of the test strip 50 partially across the restrictor port 40 but above the bottom 43 of the test strip chamber 26 means that the test strip 50 is exposed to the liquid passing through the restrictor port 40, but the test strip 50 does not necessarily sit in the residue that gathers at the bottom 43 test strip chamber 26.

Figure 7:
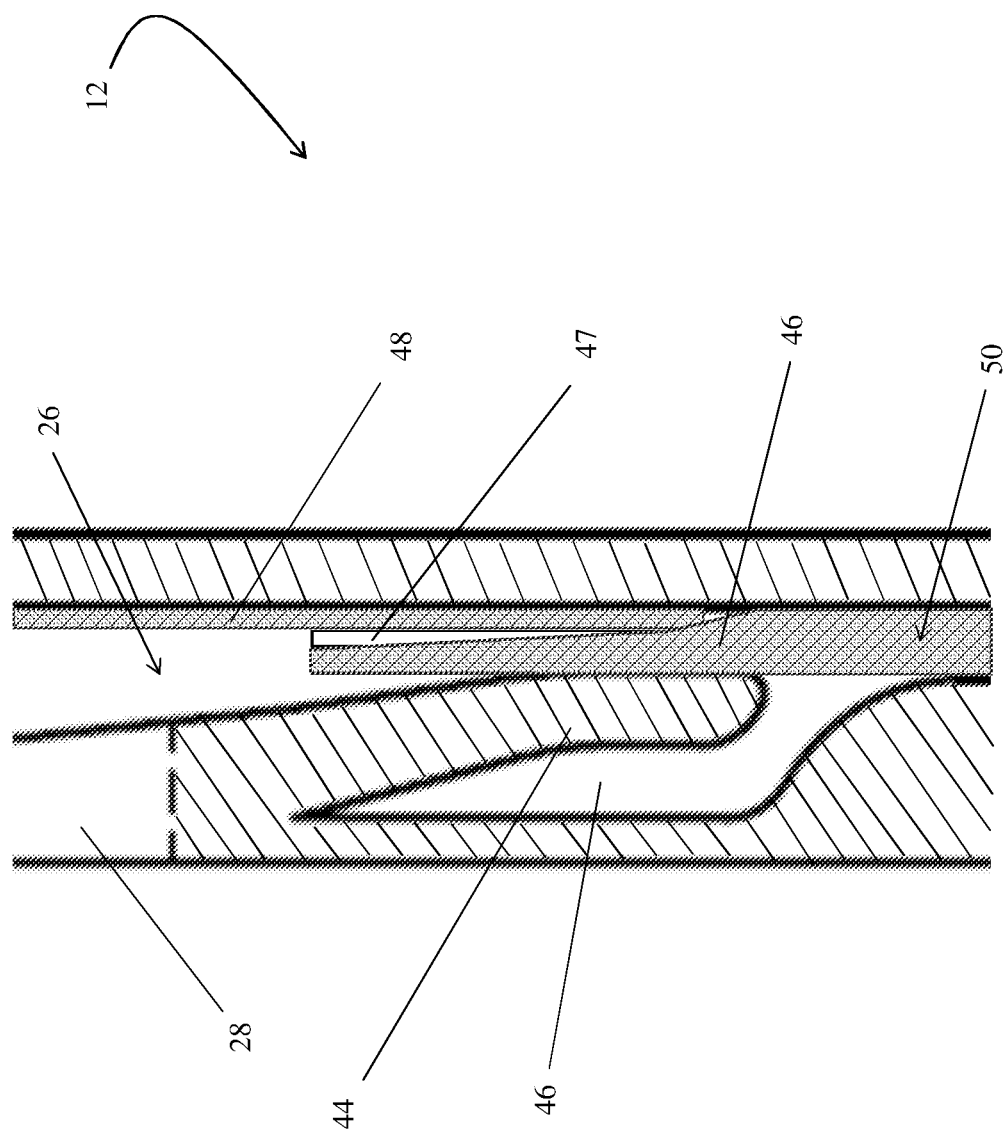
FIG. 7 is an enlarged cross section showing the flex plate contacting the test strip.

As shown in FIGS. 3, 6, and 7, a flex plate 44 is positioned above the restrictor port 40 and below the test window 28 on a front portion 30 of the sleeve 12. The flex plate 44 is comprised of a self-adjusting resilient material. For the purposes of this disclosure, the term "resilient" means rigid but capable of bending/flexing significantly without breaking. In the preferred embodiment, the flex plate 44 is angled downwardly from a vertical interior wall of the test strip chamber 26 and has a generally peninsular/elongated cross section. In the preferred embodiment, the flex strip 44 extends downwardly into the test strip chamber 26 at an angle of about 14 degrees. The flex plate has a horizontal width of about 4.6 mm, and a downwardly-angled length of about 7 mm. In alternative embodiments, the flex plate 44 may have a generally ">" shape where the nose of the ">" contacts the test strip.

As best shown in FIGS. 6 and 7, the flex plate 44 holds the test strip 50 in place—but does not exert enough force on the test strip 50 to damage the test strip 50 materials or impair the test strip's 50 function. The flex plate 44 is sufficiently flexible to allow for different material tolerance thicknesses used in test strip 50 construction—which facilitates the transfer of chemical reagents between the separate material components of a test strip 44. The flex plate 44 is also designed to limit excess liquid flow vertically up the test strip 50 or outside of the test strip, which may skew the test results. The area 46 behind the flex plate 44 comprises an overflow zone where the excess fluid may collect without impairing the test process.

As best shown in FIG. 7, in the preferred embodiment, the flex plate 44 abuts and exerts pressure on a transitional area of the test strip 50. Specifically, on a standard test strip 50, the flex plate 44 exerts pressure on the area of the test strip where the sample pad 46, the conjugate release pad 47, and the nitrocellulose membrane 48 overlap and interface. The self-adjusting pressure of the flex plate 44 ensures solid contact and fluidic communication between the three layers 46, 47, 48 so that test liquid is successfully transferred. The pressure plate 44 ensures (to the extent practical) capillary flow dictated by the porous desiccated materials that comprise test strip layers 46, 47, 48. Test liquid will continue to flow through the nitrocellulose membrane 28 to another material (not shown) at the top of the test strip 50 that serves as an absorbent sink which, when saturated, ends the capillary draw and prevents backflow action.

In operation, in the preferred embodiment, a user breaks the frangible seal 24 (if there is one) or unscrews the sealing cap on the top capsule 16 and adds a sample material (which may be solid or liquid) to the capsule 16. The user may use the (for example) scoop 36 on the bottom of the cap 32 to break the seal and/or prepare the sample material. Depending on the nature of the test, the capsule 16 may or may not hold a buffer fluid or other media required for the test. For example, in the case of a simple urine test, a urine sample is added directly to an empty capsule 16. When the sample preparation is complete, the cap 32 is screwed (or otherwise connected) to the capsule 16.

To initiate the test, a user screws the capsule 16 down into the sleeve 12 so that a spike 38 pierces the bottom 22 of the capsule 16 and an analyte liquid (or a solid-liquid mix) flows out of the capsule, through the restrictor port 40, and into the bottom 41 of the sleeve 12. As liquid continues to flow from the capsule 16, the liquid flows through the restrictor port 40 and into the bottom 43 of the test strip chamber 26. The restrictor port 40, in combination with the test strip chamber 26 and the bottom portion of the test strip 50—forms a structure that functions to create a capillary force that "wicks" fluid from the capsule 16 in the central interior opening 14 through the restrictor port 40 and upwardly to the test strip 50.

The liquid in the test strip 50 is drawn upwardly (by capillary action) until the liquid reaches a position adjacent to the flex plate 44. The flex plate 44 exerts sufficient pressure on the test strip 50 to maintain the position and stability of the test strip 50 and facilitate the transfer of analyte liquid between test strip materials. The liquid continues to flow upwardly until the liquid reaches a position corresponding to an absorbent pad at the top of the test strip. Test results are resolved on the test strip 50 and are interrogated at the test window 28, where the presence or absence of a target analyte is generally indicated by a visual indicator system, thereby completing the test. A user then reads the results of the test (as indicated on the test strip) either directly with his eyes, or electronically with a digital scanner/camera/reader.

Figure 8:
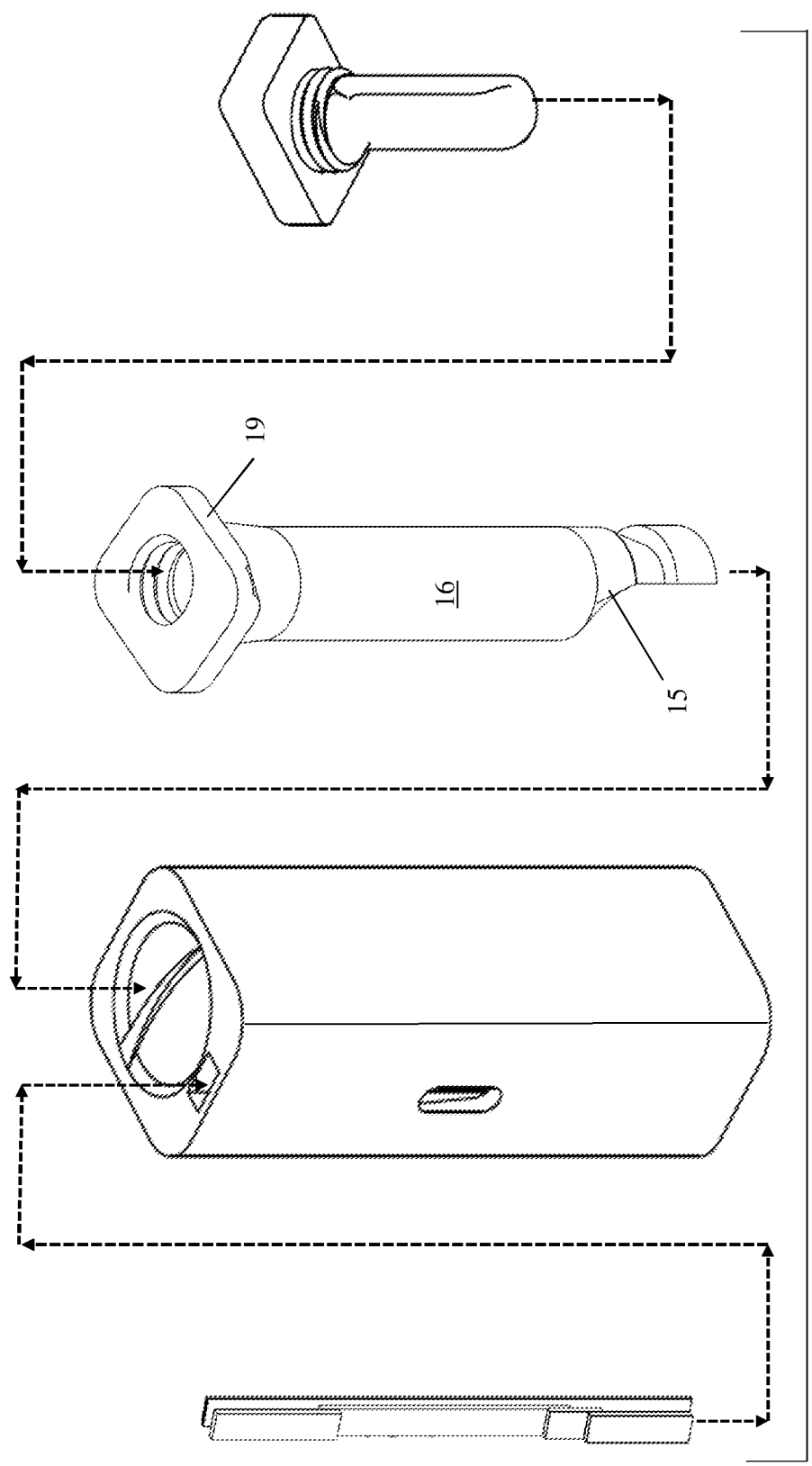
FIGS. 8 and 9 show an alternative embodiment.
Figure 9:
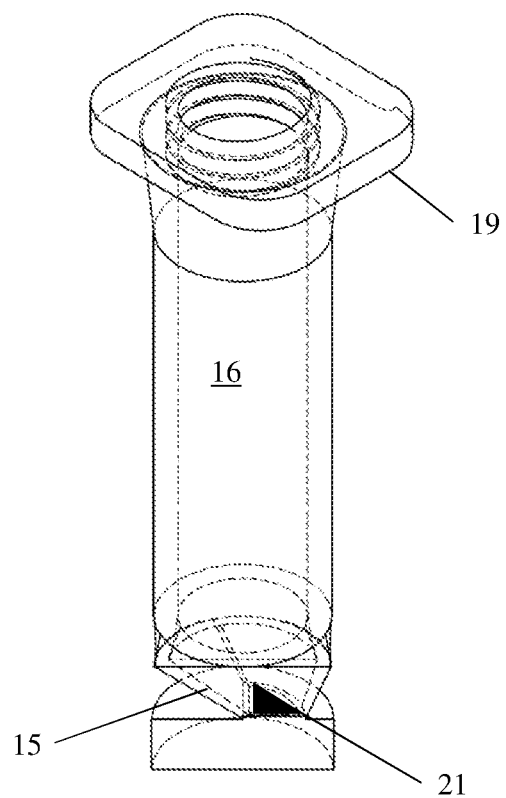

FIGS. 8 and 9 show an alternative embodiment of the system 10. This embodiment involves breaking the bottom of the capsule rather than puncturing to allow fluid to flow. This allows the capsule to be seated and integrated within the housing with no parts in the base of the sleeve 12 sticking out and interfering with the flow of the fluid from the capsule 16.

As best shown in FIG. 9, in the alternative embodiment, the bottom 15 of the capsule 16 is angled so that liquid flowing out of the capsule 16 is funneled out of a single break area 21 at the lowest point (the base) of capsule 16. The smaller thin-walled area 21 allows a user to break the area upon twisting. The bottom of the sleeve 12 is modified to accommodate the alternative capsule design, with the bottom plug of the capsule (portion below 21) seated in place within the bottom of the housing when the user twists, forcing the break of the weak point 21.

As shown in FIGS. 8 and 9, the alternative capsule 16 further includes a shoulder 19 to make handling of the capsule 16 easier. Additionally, unlike the preferred embodiment, there are no threads or grooves on the capsule 16 or in the interior of the sleeve 12—the capsule is seated fully within the housing. The test is initiated by a twist, forcing the capsule 16 to break as described above. Once the bottom of the capsule 16 is broken and the test is initiated, the test process proceeds as described above.

Figure 10:
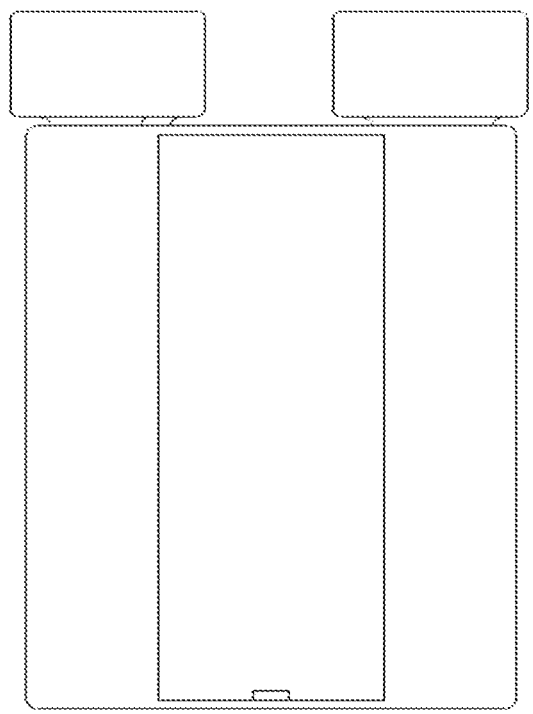
FIGS. 10 and 11 show a further alternative embodiment.
Figure 11:
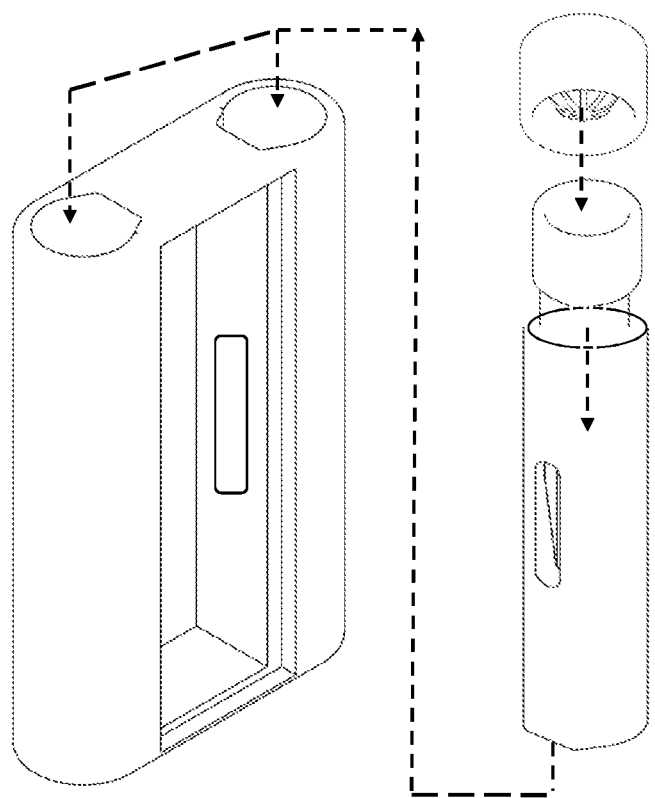

FIGS. 10 and 11 shows a simplified alternative compact design that allows a user to carry multiple test sleeves.

For the foregoing reasons, it is clear that the method and apparatus described herein provides an innovative modular biosensor system 10 that may be used in multiple applications. The current system 10 may be modified in multiple ways and applied in various technological applications. The disclosed method and apparatus may be modified and customized as required by a specific operation or application, and the individual components may be modified and defined, as required, to achieve the desired result.

Although the materials of construction are generally assumed to be various plastics, they may include a variety of compositions consistent with the function described herein. Such variations are not to be regarded as a departure from the spirit and scope of this disclosure, and all such modifications as would be obvious to one skilled in the art are intended to be included within the scope of the following claims.

The amounts, percentages and ranges disclosed herein are not meant to be absolutely limiting, and increments between the recited amounts, percentages and ranges are specifically envisioned as part of the invention. All ranges and parameters disclosed herein are understood to encompass any and all sub-ranges subsumed therein, and every number between the endpoints. For example, a stated range of "1 to 10" should be considered to include any and all sub-ranges between (and inclusive of) the minimum value of 1 and the maximum value of 10 including all integer values and decimal values; that is, all sub-ranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Similarly, if the term "about" precedes a numerically quantifiable measurement, that measurement is assumed to vary by as much as 10%. Essentially, as used herein, the term "about" refers to a quantity, level, value, or amount that varies by as much 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein). The invention illustratively disclosed herein suitably may be practiced in the absence of any element which is not specifically disclosed herein.

What is claimed is:

1. A biosensor system comprising:
a sleeve having a capsule opening and a test strip chamber;
a capsule configured to slide into the sleeve capsule opening;
a test strip configured to slide into the test strip chamber; and,
a resilient flex plate extending from an interior wall of the test strip chamber, the flex plate contacting the test strip thereby structurally facilitating a liquid transfer between independent test strip materials and maintaining the test strip in position;
wherein the system is structured so that as a user ruptures a bottom portion of the capsule, an analyte liquid flows from the capsule and to a bottom of the test strip, and then upwardly past the flex plate so that results of the test are shown on the test strip.

2. The system of claim 1 further comprising a restrictor port, the restrictor port being positioned between the capsule opening and the test strip chamber.

3. The system of claim 2 wherein the restrictor port in combination with the test strip chamber and a bottom portion of the test strip, forms a structural relationship that functions to create a capillary force that wicks analyte from the capsule through the restrictor port and up the test strip.

4. The system of claim 2 wherein the test strip at least partially blocks the restrictor port.

5. The system of claim 2 wherein the restrictor port abuts the test strip.

6. The system of claim 2 wherein the restrictor port is positioned above a bottom of the test strip chamber.

7. The system of claim 1 wherein the capsule opening and the test strip chamber are elongated and extend parallel to one another.

8. The system of claim 1 further comprising a test window, the test window comprising an aperture in the sleeve, the aperture being positioned so that a user can see through the sleeve and observe the test strip in the test strip chamber, and thereby observe a result of the test.

9. The system of claim 1 wherein the capsule comprises a thread or groove, and the capsule opening in the sleeve comprises a corresponding thread or groove, so that a test is initiated when a user screws the capsule into the sleeve and ruptures the capsule.

10. The system of claim 1 wherein the capsule contains a liquid or a solid with a liquid buffering solution.

11. The system of claim 1 further comprising a cap configured to fit onto the capsule, the bottom of the cap comprising a scoop.

12. The system of claim 1 wherein the system further comprises a spike in a bottom of the sleeve, whereby a test is initiated when the spike ruptures a bottom of the capsule.

13. The system of claim 1 wherein the system is structured so that the flex plate applies pressure on an area of the test strip where portions of test strip material overlap and/or interface.

14. The system of claim 1 wherein the test strip comprises a paper strip having a sample pad, a conjugate release pad, and a nitrocellulose membrane.

15. The system of claim 1 wherein the test strip comprises a paper strip having a sample pad, a conjugate release pad, and a nitrocellulose membrane, the flex plate applying pressure in an area where the sample pad, a conjugate release pad, and a nitrocellulose membrane overlap and/or interface.

16. The system of claim 2 wherein a bottom of the sleeve is angled downwardly so that, when a test is initiated, a punctured portion of the capsule faces toward the restrictor port.

17. The system of claim 1 wherein the flex plate maintains the test strip in position and applies enough pressure to facilitate liquid movement between test strip materials but not prevent movement of the liquid up the test strip.

18. The system of claim 1 wherein the flex plate extends downwardly into the test strip chamber and has a generally peninsular/elongated cross section.

19. The system of claim 1 wherein the test strip comprises an immunochromatographic test strip.

20. A method of testing a liquid analyte for a target substance, the method comprising:
    (a) providing the system of claim 1;
    (b) adding the analyte to the capsule; and
    (c) initiating a test and subsequently reading the test result from the test strip.

21. A method of testing a solid analyte for a target substance, the method comprising:
    (a) providing the system of claim 1;
    (b) combining the solid analyte with a buffering fluid to create a mix;
    (c) adding the mix to the capsule; and
    (d) initiating a test and subsequently reading the test result from the test strip.

22. A biosensor system comprising a sleeve having a capsule opening and a test strip chamber configured so that a test strip fits into the test strip chamber and a resilient flex plate abuts the test strip, wherein as an analyte fluid flows into a bottom of the sleeve, the analyte is drawn (via capillary action) upwardly into the test strip chamber and up through the test strip, the flex plate extending from an interior wall of the test strip chamber, the flex plate contacting the test strip and maintaining the test strip in position and exerting contact force between at least two test strip layers, the test strip thereby facilitating liquid analyte transfer between those test strip layers but not preventing the analyte from flowing upwardly past the flex plate so that results of the test are shown on the test strip.

* * * * *